United States Patent
Kojima et al.

(10) Patent No.: US 9,320,727 B2
(45) Date of Patent: Apr. 26, 2016

(54) COMBINATIONS OF SGLT 2 INHIBITORS AND ANTIHYPERTENSIVE DRUGS

(71) Applicant: TAISHO PHARMACEUTICAL CO., LTD, Tokyo (JP)

(72) Inventors: Naoki Kojima, Tokyo (JP); Richard J. Roman, Brandon, MS (US); Noriyuki Miyata, Tokyo (JP); Teisuke Takahashi, Tokyo (JP); Hideki Tomoike, Tokyo (JP); Takuya Takeda, Tokyo (JP)

(73) Assignee: TAISHO PHARMACEUTICAL CO., LTD, Tokyo (JP)

( * ) Notice: Subject to any disclaimer, the term of this patent is extended or adjusted under 35 U.S.C. 154(b) by 0 days.

(21) Appl. No.: 14/424,096

(22) PCT Filed: Aug. 30, 2013

(86) PCT No.: PCT/JP2013/073300
§ 371 (c)(1),
(2) Date: Feb. 26, 2015

(87) PCT Pub. No.: WO2014/034842
PCT Pub. Date: Mar. 6, 2014

(65) Prior Publication Data
US 2015/0320721 A1    Nov. 12, 2015

Related U.S. Application Data

(60) Provisional application No. 61/695,016, filed on Aug. 30, 2012.

(51) Int. Cl.
*A61K 31/382* (2006.01)
*A61K 31/40* (2006.01)
*A61K 31/41* (2006.01)
*A61K 31/401* (2006.01)
*A61K 45/06* (2006.01)

(52) U.S. Cl.
CPC ............... *A61K 31/382* (2013.01); *A61K 31/40* (2013.01); *A61K 31/401* (2013.01); *A61K 31/41* (2013.01); *A61K 45/06* (2013.01)

(58) Field of Classification Search
None
See application file for complete search history.

(56) References Cited

U.S. PATENT DOCUMENTS

| 6,515,117 B2 | 2/2003 | Ellsworth et al. |
| 2006/0074031 A1 | 4/2006 | Eckhardt et al. |
| 2008/0132563 A1 | 6/2008 | Kakinuma et al. |

FOREIGN PATENT DOCUMENTS

| JP | 2003-511458 A | 3/2003 |
| JP | 2008-31161 A | 2/2008 |
| JP | 2008-514668 A | 5/2008 |
| WO | 01/27128 A1 | 4/2001 |
| WO | 2006/073197 A1 | 7/2006 |
| WO | 2010048358 A2 | 4/2010 |
| WO | 2010119990 A1 | 10/2010 |
| WO | 2010138535 A1 | 12/2010 |

OTHER PUBLICATIONS

Kojima et al., "Effects of a New SGLT2 Inhibitor, Luseogliflozin, on Diabetic Nephropathy in T2DN Rats," Journal of Pharmacology and Experimental Therapeutics, Jun. 2013, vol. 345, pp. 464-472 (9 pages total).
Seino, Y. et al., "A Novel Potent and Highly Selective Renal Sodium-glucose Co-transporter 2 (SGLT2) Inhibitor, TS-71, Improves Glycaemic Control and Lowers Body Weight in Japanese Patients with Type 2 Diabetes Mellitus," Diabetologia, 2011, vol. 54, Supplement 1, p. S68, Abstract No. 148 (3 pages total).
Seino et al., "Luseogliflozin (TS-071), a Selective SGLT2 Inhibitor. Improves Glycemic Control and Lowers Body Weight in Japanese Patients With Type 2 Diabetes Mellitus," Diabetes, 2012.06, vol. 61, Suppl. 1, p. A266-A267, Abstract No. 1039-P.
Kojima et al., "Renoprotective Effects of SGLT2 Inhibitor, Luscogliflozin on the Progression of Diabetic Nephropathy in T2DN Rats," Hypertension, Sep. 2012, vol. 60, No. 3, Supp. Meeting Abstracts, Abstract No. 221.
International Preliminary Report on Patentability dated Mar. 3, 2015 from the International Searching Authority in counterpart application No. PCT/JP2013/073300.
Seino et al., "TS-071, a Novel and Selective SGLT2 Inhibitor, Improved Glycemic Control and Decreased Body Weight in 12-Week Study of Japanese Patients with Type 2 Diabetes Mellitus," Diabetes, 2011, vol. 60, Suppl. 1, p. A274, Abstract No. 998-P.
An Invitation to Respond to Written Opinion dated Dec. 22, 2015 from the Intellectual Property Office of Singapore in counterpart application No. 11201501510S.
Ghosh, R. K. et al., "SGLT2 inhibitors: A new emerging therapeutic class in treatment of type 2 diabetes mellitus". Journal of Clinical Pharmacology, May 4, 2011, vol. 52, No. 4, pp. 457-463.
Osorio, H. et al., "Effects of Phlorizin on SGLT2 expression in the kidney of diabetic rats". Journal of Nephrology, Oct. 31, 2010, vol. 23, No. 05, pp. 541-546.
Osorio, H. et al., "Effect of treatment with Losartan on salt sensitivity and SGLT2 expression in hypertensive diabetic rats". Diabetes Research and Clinical Practice, Oct. 2, 2009, vol. 86, pp. e46-e49.
Communication dated Jan. 25, 2016, from the European Patent Office in counterpart European Application No. 13832429.8.

*Primary Examiner* — Brian J Davis
(74) *Attorney, Agent, or Firm* — Sughrue Mion, PLLC

(57) ABSTRACT

Medicaments that depend on a combination of SGLT 2 inhibitors and antihypertensive drugs and which are useful in the treatment of diseases involving at least hypertension or diabetes mellitus as a risk factor of cardiovascular events, as well as methods of treating the diseases are provided. Since the present invention exhibits a superior hypotensive action that cannot be attained by any single antihypertensive drugs, the conventional problems associated with the use of two or more antihypertensive drugs in order to lower the blood pressure to the desired level can be solved. In addition, the present invention shows a marked therapeutic efficacy in diabetes mellitus, a disease associated with diabetes mellitus, or complications of diabetes mellitus, in particular, diabetic nephropathy. As a further advantage, the present invention is also useful for the treatment of diseases involving lowered renal function.

9 Claims, 4 Drawing Sheets

*: P<0.05 vs. pathological control group (multiple comparison test)

: P<0.05 vs. compound A dosed group (multiple comparison test)

$: P<0.05 vs. lisinopril dosed group (multiple comparison test)

*: $P<0.05$ vs. pathological control group (multiple comparison test)

: $P<0.05$ vs. compound A dosed group (multiple comparison test)

$: $P<0.05$ vs. lisinopril dosed group (multiple comparison test)

*: P<0.05 vs. pathological control group (multiple comparison test)

: P<0.05 vs. compound A dosed group (multiple comparison test)

$: P<0.05 vs. lisinopril dosed group (multiple comparison test)

**: P<0.01 vs. pathological control group (Student's t-test)

**: P<0.01 vs. compound A dosed group (Student's t-test)

$: P<0.01 vs. valsartan dosed group (Student's t-test)

COMBINATIONS OF SGLT 2 INHIBITORS AND ANTIHYPERTENSIVE DRUGS

CROSS REFERENCE TO RELATED APPLICATIONS

This application is a National Stage of International Application No. PCT/JP2013/073300 filed Aug. 30, 2013, claiming priority based on US Provisional Application No. 61/695,016 filed Aug. 30, 2013, the contents of all of which are incorporated herein by reference in their entirety.

TECHNICAL FIELD

The present invention relates to combinations of SGLT 2 inhibitors and antihypertensive drugs. The present invention more specifically relates to medicaments useful in the treatment of diseases involving at least hypertension or diabetes mellitus as a risk factor of cardiovascular events, as well as methods for treating such diseases.

BACKGROUND ART

Hypertension and diabetes mellitus are risk factors for the onset of cardiovascular events (e.g., myocardial infarction, angina pectoris, congestive heart failure, cerebral infarction, and transient cerebral ischemic attack); the onsets of diabetes mellitus and hypertension often overlap to promote the onset of cardiovascular events and induce serious diseases that may directly lead to death.

It is therefore important to repress the onset and progression of cardiovascular events by performing appropriate treatments on diabetes mellitus and hypertension after identifying their pathologic conditions.

Diabetes mellitus is a metabolic syndrome that involves chronic high blood glucose levels caused by impaired insulin secretion or impaired insulin action in the target organ. The pathologic condition of diabetes mellitus is complex and involves not only abnormal glucose metabolism but also abnormalities in lipid metabolism and the circulatory system. As a consequence, a variety of complications often accompany the progress of diabetes mellitus. Typical complications of diabetes mellitus are diabetic retinopathy, nephropathy, and neuropathy. In particular, diabetic nephropathy causes glomerular excessive filtration or glomerular enlargement in the early stage of onset, followed by decreased cell counts due to inflammation and apoptosis, eventually leading to end-stage renal failure due to glomerular hardening and interstitial fibrosis.

Drugs currently used to treat diabetes mellitus include biguanides, sulfonylureas, glycosidase inhibitors, insulin tolerance ameliorators, dipeptidyl dipeptidase IV (DPP-IV) inhibitors, etc. In addition, sodium-dependent glucose cotransporter-2 (SGLT-2) inhibitors have also been developed as drugs for treating diabetes mellitus via a new mechanism.

The treatment of diabetes mellitus, however, extends so long that side effects often raise a problem and particularly in the case of diabetic nephropathy involving a lowered renal function, many diabetic drugs are difficult to administer in the first place since problems with drug pharmacokinetics (clearance pathway) increase the concern of side effects. Some drugs exhibit a certain level of therapeutic efficacy for diabetic nephropathy if it is at a mild stage but no drugs are yet known that have therapeutic efficacy even after the disease has progressed to the stage of interstitial fibrosis.

Hypertension not only promotes arteriosclerosis but also causes ventricular remodeling due to enlargement of the left ventricle, so it plays a primary role in the onset of cardiovascular events. Therefore, an appropriate hypotensive treatment is required to repress the onset and progression of cardiovascular events and provide improved prognosis for a longer period. To provide an appropriate hypotensive treatment, it is important to have a risk assessment after identifying the pathologic condition and impaired organ of the patient, selecting an appropriate antihypertensive drug, and attaining blood pressure targets. Patients with hypertension complicated by impaired organs as in diabetes mellitus and chronic kidney disease are diagnosed as constituting a group with high risk of cardiovascular events and require strict lowering of blood pressure (Guidelines for the Management of Hypertension 2009 or JSH2009 for short, published by the Japanese Society of Hypertension). Currently, however, it is difficult to attain lower blood pressure targets with single antihypertensive drugs and combination therapy using two or more drugs is required. The problem is that since the treatment is prolonged, side effects due to combined drug use may sometimes occur. For instance, it has been reported that combinations of diuretics and β-blockers adversely affect glycolipid metabolism or that combinations of ACE inhibitors and angiotensin II receptor blockers (ARBs) have high likelihood of transition to end-stage renal failure.

It is therefore necessary to resolve the above-mentioned problems with the combined use of antihypertensive drugs. As of today, no single antihypertensive drugs have been reported that can attain that lower blood pressure targets that are required to repress the onset and progression of cardiovascular events.

SUMMARY OF INVENTION

Technical Problem

An object of the present invention is to provide medicaments useful in the treatment of diseases involving at least hypertension or diabetes mellitus as a risk factor of cardiovascular events, as well as methods for treating such diseases.

Another object of the present invention is to provide medicaments that can attain the lower blood pressure targets required to repress the onset and progression of cardiovascular events without the problem of side effects, or to provide treatment methods for attaining the lower blood pressure targets.

Yet another object of the present invention is to provide medicaments useful in the treatment of diabetes mellitus, diseases associated with diabetes mellitus or complications of diabetes mellitus, in particular, diabetic nephropathy, or methods of treating such diseases.

Still another object of the present invention is to medicaments useful in the treatment of a disease further involving a lowered renal function, or a method of treating the disease.

Solution to Problem

The present inventors conducted intensive studies on medicaments that would attain the above-stated objects and found that SGLT 2 inhibitors, although not having any observable blood pressure lowering action upon independent administration, showed an unexpected effect of enhancing the blood pressure lowering action of antihypertensive drugs with which they were combined; the present invention has been accomplished on the basis of this finding. The present inventors found that the combination of SGLT 2 inhibitors with antihypertensive drugs brought about quite unexpected and marked effects as compared with the case where they were used independently in the treatment of diabetes mellitus, diseases associated with diabetes mellitus or complications of diabetes mellitus, in particular, diabetic nephropathy.

To be more specific, the present invention can be implemented in the following modes.

(1) A medicament for treating a disease involving at least hypertension or diabetes mellitus as a risk factor of cardiovascular events, which is characterized by a combination of an SGLT 2 inhibitor and an antihypertensive drug.

(2) The medicament as recited in (1), wherein the SGLT 2 inhibitor is a 1-thio-D-glucitol compound represented by the below-indicated general formula (I), a pharmaceutically acceptable salt thereof, or a hydrate of the compound or salt:

[Formula 1]

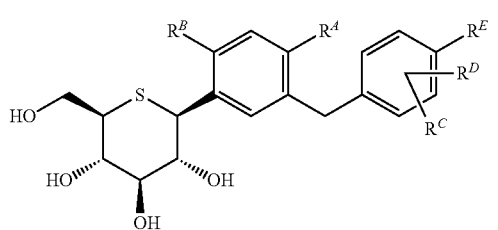

(I)

[in formula (I),
$R^A$ represents a hydrogen atom, a $C_{1-6}$ alkyl group, —$OR^F$, or a halogen atom;
$R^B$ represents a hydrogen atom, a hydroxy group, or —$OR^F$;
$R^C$ or $R^D$, which may be the same or different, each represent a hydrogen atom, a halogen atom, a $C_{1-8}$ alkyl group, or —$OR^F$,
$R^E$ represents (i) a hydrogen atom, (ii) a halogen atom, (iii) a hydroxy group, (iv) a $C_{1-8}$ alkyl group optionally substituted by a halogen atom, (v) —$OR^F$, or (vi) —$SR^F$, with $R^F$ representing a $C_{1-6}$ alkyl group optionally substituted by a halogen atom.]

(3) The medicament as recited in (2), wherein the 1-thio-D-glucitol compound is a compound selected from the group consisting of:
(1 S)-1,5-anhydro-1-[3-(4-ethoxybenzyl)-6-methoxy-4-methylphenyl]-1-thio-D-glucitol;
(1 S)-1,5-anhydro-1-[4-chloro-3-(4-methylbenzyl)phenyl]-1-thio-D-glucitol;
(1S)-1,5-anhydro-1-[4-chloro-3-(4-methylthiobenzyl)phenyl]-1-thio-D-glucitol; and
(1S)-1,5-anhydro-1-[4-chloro-3-(4-ethylbenzyl)phenyl]-1-thio-D-glucitol.

(4) The medicament as recited in (2) or (3), wherein the 1-thio-D-glucitol compound is (1S)-1,5-anhydro-1-[3-(4-ethoxybenzyl)-6-methoxy-4-methylphenyl]-1-thio-D-glucitol.

(5) The medicament as recited in any one of (1) to (4), wherein the antihypertensive drug is a suppressor of the renin-angiotensin-aldosterone system.

(6) The medicament as recited in (5), wherein the suppressor of the rennin-angiotensin-aldosterone system is an ACE inhibitor or an angiotensin II receptor blocker.

(7) The medicament as recited in (6), wherein the ACE inhibitor is a compound selected from the group consisting of alacepril, benazepril, captopril, ceronapril, cilazapril, delapril, enalapril, enalaprilat, fosinopril, imidapril, lisinopril, moveltipril, moexipril, perindopril, quinapril, ramipril, spirapril, temocapril, and trandolapril, or a pharmaceutically acceptable salt thereof, or a hydrate of the compound or salt.

(8) The medicament as recited in (6), wherein the angiotensin II receptor blocker is a compound selected from the group consisting of losartan, candesartan, irbesartan, valsartan, telmisartan, and eprosartan, or a pharmaceutically acceptable salt thereof, or a hydrate of the compound or salt.

(9) The medicament as recited in (1), wherein the disease is hypertension.

(10) The medicament as recited in (1), wherein the disease is diabetes mellitus, a disease associated with diabetes mellitus, or a complication of diabetes mellitus.

(11) The medicament as recited in any one of (1) to (10), wherein the disease involves the manifestation of both diabetes mellitus and hypertension.

(12) The medicament as recited in any one of (1) to (11), wherein the disease is diabetic nephropathy.

(13) The medicament as recited in any one of (1) to (11), wherein the disease further involves an observable lowered renal function.

(14) The medicament as recited in any one of (1) to (13) for treating a disease involving at least hypertension or diabetes mellitus as a risk factor of cardiovascular events, which is characterized in that an SGLT 2 inhibitor and an antihypertensive drug are administered to a patient either simultaneously or separately.

(15) The medicament which comprises an SGLT 2 inhibitor and is used in combination with an antihypertensive drug to thereby enhance the hypotensive action of the antihypertensive drug.

(16) The medicament which comprises an SGLT 2 inhibitor and is used in combination with an antihypertensive drug to thereby enhance the effect of the SGLT 2 inhibitor in treating diabetes mellitus, a disease associated with diabetes mellitus, or a complication of diabetes mellitus.

(17) The medicament which comprises an SGLT 2 inhibitor and is used in combination with an antihypertensive drug to thereby enhance the effect of the SGLT 2 inhibitor in treating diabetic nephropathy.

(18) A method for treating a disease involving at least hypertension or diabetes mellitus as a risk factor of cardiovascular events, which comprises administering an SGLT 2 inhibitor and an antihypertensive drug, either simultaneously or separately, to a patient in need thereof.

Advantageous Effects of Invention

The combination of an SGLT 2 inhibitor and an antihypertensive drug according to the present invention showed an unexpected effect in that the blood pressure lowering action of the antihypertensive drug on its own was enhanced although no blood pressure lowering action was observed when the SGLT 2 inhibitor was administered alone. In addition, the SGLT 2 inhibitor and the antihypertensive drug combined together showed better therapeutic effects for diabetic nephropathy than when the respective drugs were administered individually. Of particular interest was that although the antihypertensive drug administered alone provided no observable effect on the progress of renal fibrosis, the action of the SGLT 2 inhibitor on its own for repressing the progress of renal fibrosis was enhanced when it was used in combination with the antihypertensive drug, and this was a quite unexpected effect.

DESCRIPTION OF EMBODIMENTS

Figure 1:
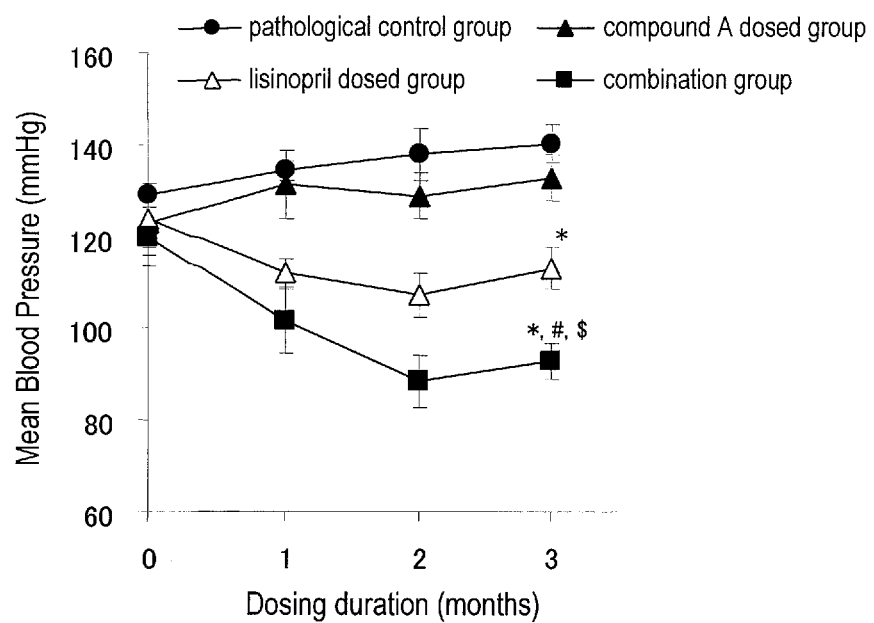
FIG. 1 compares how hypertension could be alleviated by administering Compound A or lisinopril alone, or administering Compound A and lisinopril in combination.

The terminology as used herein has the following meanings.

The "SGLT 2 inhibitor" is a drug that inhibits the exchange between sodium and glucose in the sodium-dependent glucose cotransporter-2 (SGLT-2) so as to suppress an increase in the glucose concentration in the blood. Blood glucose lowering effect can also reduce the burden on β cells in exhausted islets of Langerehans in the pancreas, thereby recovering their insulin secreting ability. As another advantage, glucose toxicity is alleviated by blood glucose lowering effect, whereupon an insulin resistance reducing action is manifested.

SGLT 2 inhibitors that can be used include, for example, dapagliflozin, ipragliflozin, tofogliflozin, empagliflozin, canagliflozin, etc.

SGLT 2 inhibitors that can also be used include 1-thio-D-glucitol compounds represented by general formula (I) set forth above, pharmaceutically acceptable salts thereof, or hydrates of the compounds or salts.

Methods for producing the 1-thio-D-glucitol compounds represented by general formula (I), or pharmaceutically acceptable salts thereof, or hydrates of the compound or salts are disclosed in the international publication WO 2006/073197 A1.

The "$C_{1-6}$ alkyl group" refers to linear or branched alkyl groups having 1-6 carbon atoms and examples include a methyl group, an ethyl group, a n-propyl group, an isopropyl group, a n-butyl group, an isobutyl group, a tert-butyl group, a sec-butyl group, a n-pentyl group, a tert-amyl group, a 3-methylbutyl group, a neopentyl group, and a n-hexyl group.

The "halogen atom" may be a fluorine atom, a chlorine atom, a bromine atom, or an iodine atom.

The "pharmaceutically acceptable salts" may include but are not limited to the following: salts with inorganic acids such as sulfuric acid, hydrochloric acid, hydrobromic acid, phosphoric acid, and nitric acid; salts with organic acids such as acetic acid, oxalic acid, lactic acid, tartaric acid, fumaric acid, maleic acid, citric acid, benzenesulfonic acid, methanesulfonic acid, p-toluenesulfonic acid, benzoic acid, camphor sulfonic acid, ethanesulfonic acid, glucoheptonic acid, gluconic acid, glutamic acid, glycolic acid, malic acid, malonic acid, mandelic acid, galactaric acid, and naphthalene-2-sulfonic acid; salts with one or more metallic ions such as lithium ion, sodium ion, potassium ion, calcium ion, magnesium ion, zinc ion, and aluminum ion; salts with amines such as ammonia, arginine, lysine, piperazine, choline, diethylamine, 4-phenylcyclohexylamine, 2-aminoethanol, and benzathine.

Among the 1-thio-D-glucitol compounds represented by formula (I), the following are preferred ones from the viewpoint of showing superior SGLT 2 inhibitory activity:

(1 S)-1,5-anhydro-1-[3-(4-ethoxybenzyl)-6-methoxy-4-methylphenyl]-1-thio-D-glucitol;

(1 S)-1,5-anhydro-1-[4-chloro-3-(4-methylbenzyl)phenyl]-1-thio-D-glucitol;

(1 S)-1,5-anhydro-1-[4-chloro-3-(4-methylthiobenzyl)phenyl]-1-thio-D-glucitol; and (1 S)-1,5-anhydro-1-[4-chloro-3-(4-ethylbenzyl)phenyl]-1-thio-D-glucitol.

A more preferred compound is (1S)-1,5-anhydro-1-[3-(4-ethoxybenzyl)-6-methoxy-4-methylphenyl]-1-thio-D-glucitol. The compound (1S)-1,5-anhydro-1-[3-(4-ethoxybenzyl)-6-methoxy-4-methylphenyl]-1-thio-d-glucitol is preferably a hydrate.

The compounds of formula (I) according to the present invention may also occur as various types of solvates. Alternatively, they may take the form of hydrates in order to ensure the ease of application as medicaments.

The compounds of formula (I) according to the present invention cover all conceivable forms including enantiomers, diastereomers, equilibrium compounds, mixtures thereof at any proportions, racemic modifications, etc.

Antihypertensive drugs include, but are not limited to, diuretics, calcium antagonists, suppressors of the renin-angiotensin-aldosterone system (e.g. angiotensin-converting enzyme inhibitors (ACE inhibitors), angiotensin II receptor blockers (ARB), direct renin inhibitors, and aldosterone antagonists), sympathetic nerve blockers, and α2 receptor stimulants; preferred ACE inhibitors may typically be selected from among alacepril, benazepril, captopril, ceronapril, silazapril, delapril, enalapril, enalaprilat, fosinopril, imidapril, lisinopril, moveltipril, moexipril, perindopril, quinapril, ramipril, spirapril, temocapril, and trandolapril, as well as all stereoisomers thereof, or pharmaceutically acceptable salts of those compounds or their stereoisomers, or hydrates of the compounds, stereoisomers or salts.

Angiotensin II receptor blockers may typically be selected from among losartan, candesartan, irbesartan, valsartan, telmisartan, and eprosartan, as well as all stereoisomers thereof, or pharmaceutically acceptable salts of those compounds or their stereoisomers, or hydrates of the compounds, stereoisomers or salts.

The present invention relates to medicaments useful for the treatment of diseases involving at least hypertension or diabetes mellitus as a risk factor of cardiovascular events, or methods for treating such diseases.

The "cardiovascular events" refers to myocardial infarction, angina pectoris, congestive heart failure, cerebral infarction, transient cerebral ischemic attacks, etc.

"Diseases involving at least hypertension or diabetes mellitus as a risk factor of cardiovascular events" include hypertension, diabetes mellitus, diseases associated with diabetes mellitus, complications of diabetes mellitus, and diseases which involve the manifestation of both hypertension and diabetes mellitus. Also embraced are diseases that further involve a lowered renal function resulting from the diseases mentioned above.

"Diabetes mellitus" is a metabolic syndrome in which chronic hyperglycemia is caused by impaired insulin secretion or impaired insulin action in the target organ. The term "hyperglycemia" herein used means that the subject is in either one of the following states: (1) the fasting plasma glucose level is 126 mg/dL or higher; (2) the level two hours after challenge with 75 g of glucose (OGTT) is 200 mg/dL or higher; (3) the postprandial plasma glucose is 200 mg/dL or higher; or (4) HbA1c is 6.5% or higher. "Diabetes mellitus" encompasses type 1 diabetes, type 2 diabetes, and other types of diabetes due to specific causes. Type 2 diabetes is preferred as a disease to be treated by the medicaments of the present invention.

The "diseases associated with diabetes mellitus" refers to disorders that are either incidental to, or caused by, or consequent to hyperglycemia; examples include obesity, hyperinsulinemia, impaired glucose metabolism, metabolic syndrome, hyperlipidemia, hypercholesterolemia, hypertriglyceridemia, impaired lipid metabolism, hypertension, congestive heart failure, edema, hyperuricemia, gout, etc. Hypertension is preferred as a disease to be treated by the medicaments of the present invention.

"Complications of diabetes mellitus" are classified as acute or chronic complications.

"Acute complications" include, but are not limited to, hyperglycemia (e.g. ketoacidosis), hyperglycemic hyperosmolar syndrome, lactic acidosis, hypoglycemia, and infections (e.g. in the skin, soft tissues, bile ducts, respiratory tract, and urinary tract).

"Chronic complications" include, but are not limited to, microangiopathy (diabetic retinopathy, diabetic neuropathy, and diabetic nephropathy) and macroangiopathy (cerebrovascular disorders, ischemic heart diseases, and arterial occlusion of lower limbs). Diabetic nephropathy is preferred as a disease to be treated by the medicaments of the present invention.

The term "hypertension" includes both essential or primary hypertension for which no cause can be identified or which has two or more causes such as cardiac and vascular changes, and secondary hypertension which has identifiable specific causes. Causes of secondary hypertension include but are not limited to obesity, kidney disease, hormone abnormality, and use of certain medicaments such as oral contraceptives, corticosteroids, and cyclosporine. The term "hypertension" may be defined as a systolic blood pressure of 140 mmHg or greater and/or a diastolic blood pressure of 90 mmHg or greater.

For treatment of hypertension, normalization of blood pressure is by no means sufficient and it is important to improve long-term prognosis by repressing the onset and progression of organ disorders such as cardiomegaly and kidney disorder, or cardiovascular disease events. To this end, blood pressure levels and associated risks of cardiovascular events are assessed in individual clinical cases and blood pressure control levels are set for the purpose of repressing those risks (see Table 1 below: quoted from Guidelines for the Management of Hypertension 2009 or JSH2009 for short, published by the Japanese Society of Hypertension).

tension" as defined below. The term "prevention of hypertension" as used hereinabove means either suppressing exacerbation of the hypertensive state of a person in the condition of prehypertension (i.e., a patient who presents a systolic and a diastolic blood pressure between 120 mmHg/80 mmHg and 139 mmHg/89 mmHg) or ameliorating that hypertensive state.

The medicaments of the present invention can also be used in patients who have an observable lowered renal function due to the aforementioned diseases. If the renal function is lowered, medicament is often difficult to perform from a pharmacokinetic viewpoint (clearance pathway). The medicaments of the present invention are preferred since they can also be administered even in patients suffering from an impaired renal function as in chronic kidney disease or diabetic nephropathy.

The term "a lowered renal function" means a state where a factor associated with the renal function, for example, the glomerular filtration rate (GFR) has dropped below the normal level. GFR can be estimated from blood creatinine level, age, and gender, for example, to give the following ratings: normal ($\geq 90$ mL/min/1.73 cm$^2$); slightly lowered (60-89 mL/min/1.73 cm$^2$); moderately lowered (30-59 mL/min/1.73 cm$^2$); and highly lowered (<30 mL/min/1.73 cm$^2$).

The "medicament characterized by combination" according to the present invention may be such that the active ingredients, SGLT 2 inhibitor and antihypertensive drug, are formulated in a single preparation (combination drug) or separately formulated as two preparations. The produced preparations can be processed by conventional means to be made into tablets, granules, powders, capsules, emulsions, suspensions, syrups, etc. or into injections in such forms as sterile solution or suspension. In the case where the two active ingredients have been separately formulated as two preparations, the respective preparations can be administered simultaneously or separately. The medicaments according to the present invention can be administered by an oral or non-oral route to give either systemic or topical efficacy.

The medicament according to the present invention can be used in combination with other drugs for a specific purpose such as potentiating the action of the medicament or reducing

TABLE 1

Cardiovascular Risk Stratification Based on Blood Pressure (BP)

| | BP classification | | | |
| --- | --- | --- | --- | --- |
| Risk layers (Risk factors other than BP) | Prehypertension (130-139/ 85-89 mmHg) | Stage I hypertension (140-159/ 90-99 mmHg) | Stage II hypertension (160-179/ 100-109 mmHg) | Stage III hypertension ($\geq$180/$\geq$110 mmHg) |
| First risk layer (No risk factor) | No additional risk | Low risk | Medium risk | High risk |
| Second risk layer (One or two risk factors other than diabetes mellitus, as well as metabolic syndrome* are involved) | Medium risk | Medium risk | High risk | High risk |
| Third risk layer (Either one of diabetes mellitus, chronic kidney disease (CKD), organ disorder/cardiovascular disease, and 3 or more risk factors are involved) | High risk | High risk | High risk | High risk |

*Metabolic syndrome in the second risk layer is defined as follows from a precautionary viewpoint: a case where, in addition to a BP level higher than prehypertension and abdominal obesity (85 cm or above in males and 90 cm or above in females), either an abnormal plasma glucose level (110-125 mg/dL at fasting and/or impaired glucose tolerance yet to be diagnosed as diabetes mellitus) or abnormal lipid metabolism is found. A case where both are found is diagnosed as the third risk layer. If abdominal obesity and abnormal lipid metabolism are found but no other risk factor is found, the number of risk factors other than BP level is two, not three by counting in metabolic syndrome.

The "treatment of hypertension" as referred to in the present invention also encompasses the "prevention of hypertension" as referred to in the present invention also encompasses the "prevention of hyperits dosage; such other drugs include but are not limited to other drugs for the treatment of diabetes mellitus or diabetic complications, as well as anti-hyperglycemic drugs, antihypertensive drugs, antiobesity drugs, diuretics, and antithrombics. In this case, the timings at which the medicament according to the present invention and the other drugs combined therewith are to be administered are not limited in particular way and they may be administered to the subject either simultaneously or at different times. What is more, the medicament according to the present invention and the drugs combined therewith may be administered either as different preparations or as a single preparation comprising all active ingredients. The dosage of the drugs combined with the medicament according to the present invention may be chosen as appropriate, with the clinically employed dose level being taken as the reference. In addition, the proportions at which the medicament according to the present invention is combined with other drugs may be chosen as appropriate for the subject to which they are administered, the route of administration, the disease to be treated, symptoms, and the specific manner of combination.

When the medicament according to the present invention is formulated as two or more preparations containing different active ingredients, the preparations are highly likely to be administered either simultaneously or at very short intervals (successively), so it is preferred to provide precautions on documents such as package inserts or sales brochures for commercially marketed medicaments, indicating that the respective preparations are to be used in combination. It is also preferred to provide a kit having a combination of the SGLT 2 inhibitor and antihypertensive drug as a major component.

The dosage of the medicament according to the present invention varies with the subject to which it is administered, the method of administration, and so forth; in the case of oral administration, the 1-thio-D-glucitol compound is preferably administered to a patient (60 kg) at a dose of 0.1-50 mg, preferably 0.5-5 mg, more preferably 0.5-2.5 mg, per day. To give guide figures for the daily dosage of antihypertensive drugs, lisinopril may be administered at a dose of 1-20 mg, preferably 1-10 mg, more preferably 1-5 mg, and valsartan at a dose of 10-200 mg, preferably 10-100 mg, more preferably 10-30 mg.

The preparation to be formulated according to the present invention is preferably designed for oral administration, as in the form of tablets, granules, powders, capsules, emulsions, suspensions, syrups, etc. Specifically, the above-described active ingredients, either taken together or separately, are mixed with an excipient such as mannitol or lactose and the blend is granulated; the granulation may be encapsulated to make capsules or pelletized to make tablets, either on their own or after being mixed with any necessary additives for oral preparations; specific examples of such additives include but are not limited to: excipients (e.g., sugar-based or sugar alcoholic excipients such as glucose, sucrose, mannitol, lactose, xylitol, sorbitol, maltitol, and pullulan; cellulosic excipients such as microcrystalline cellulose; starch-based excipients such as corn starch; and inorganic excipients such as anhydrous calcium hydrogenphosphate); binders (e.g., cellulosic binders such as methylcellulose, hydroxypropyl cellulose, and hydroxypropyl methylcellulose); disintegrants (e.g., cellulosic disintegrants such as carmellose calcium, low-substituted hydroxypropyl cellulose, and croscarmellose sodium; and starch-based disintegrants such as partially pregelatinized starch and carboxymethyl starch sodium); fluidization agents (e.g., inorganic fluidization agents such as light anhydrous silicic acid); and lubricants (e.g., stearic acid, magnesium stearate, calcium stearate, talc, and sodium stearyl fumarate).

The proportion at which the 1-thio-D-glucitol compound according to the present invention or a pharmaceutically acceptable salt thereof or a hydrate of the compound or salt is to be combined with the antihypertensive drug varies with the type of the drugs, the subject to which the medicament is to be administered, the method of administration, and other factors; in the case of administering the medicament of the present invention to humans, one part by mass of the 1-thio-D-glucitol compound may be combined with 1-1,000 parts by mass of the antihypertensive drug to attain a better blood pressure lowering action than when the individual drugs are administered. Particularly in the case where lisinopril is used as the antihypertensive drug, it is preferred to combine one part by mass of the 1-thio-D-glucitol compound with 0.5-20 parts by mass of lisinopril. When valsartan is used as the antihypertensive drug, it is preferred to combine one part by mass of the 1-thio-D-glucitol compound with 5-200 parts by mass of valsartan. As a result, the intended effect can be attained from a smaller dose than when the individual drugs are administered. In addition, it is possible to prepare medicaments having less side effects.

The medicaments of the present invention can be prepared in accordance with the following exemplary recipes.

(Preparation 1) Tablet

Tablets were prepared, each containing the following ingredients:

| | |
|---|---|
| (1S)-1,5-anhydro-1-[3-(4-ethoxybenzyl)-6-methoxy-4-methylphenyl]-1-thio-D-glucitol (hereinafter referred to as Compound A) | 2.5 mg |
| Lisinopril hydrate | 10.9 mg (10 mg as anhydride) |
| Microcrystalline cellulose | 79.6 mg |
| D-mannitol | 95 mg |
| Carboxymethyl starch sodium | 10 mg |
| Hydroxypropyl cellulose | 10 mg |
| Magnesium stearate | 2 mg. |

(Preparation 2) Tablets

Tablets were prepared, each containing the following ingredients:

| | |
|---|---|
| Compound A | 2.5 mg |
| Valsartan | 80 mg |
| Microcrystalline cellulose | 74.5 mg |
| D-mannitol | 20 mg |
| Hydroxypropyl cellulose | 5 mg |
| Light anhydrous silicic acid | 2 mg |
| Low-substituted hydroxypropyl cellulose | 14 mg |
| Magnesium stearate | 2 mg. |

It should be noted here that Compound A is disclosed in Example 7 (as Compound 89) in WO 2006/073197 A1 and can be prepared by the method described in this publication.

EXAMPLES

Next, the present invention is described in greater detail by reference to working examples but it should be understood that the present invention is by no means limited to those examples.

<Test 1: Diabetic Nephropathy Model>

<Test Item>

The effect of compound A combined with ACE inhibitor in rats as a diabetic nephropathy model.

<Test Method>

The test was conducted with rats (T2DN rats) that were an inbred line of Goto-Kakizaki (GK) rats with a manifestation of type II diabetes mellitus and which were in an advanced stage of kidney tissue injury resulting from a long-continued diabetic condition. Rats in groups each consisting of 8-9 animals (aged 14 months on average) were given repeated doses of compound A (0.02% in mixed diet) and the ACE inhibitor lisinopril (10 mg/kg/day in drinking water), either independently or in combination, for three months. A group of rats receiving only a diet containing no compound A were pathologic controls. Before and one month after the dosing, blood pressure measurement was conducted by the tail cuff method using a noninvasive automatic hemodynamometer. After the repeated dosing, the kidneys were removed from each rat under anesthetization with ketamine and thiobutabarbital and fixed in 10% neutral buffered formalin. Thin slices of the kidneys were prepared and subjected to Masson's trichrome stain. After masking the tissue specimens, thirty glomeruli were extracted from each specimen. To quantify the morbidity of glomeruli, the extent of damage was scored on the basis of the following criteria: Grade 0: No morbidity was observed in glomeruli; grade 1: Damage was observed in 1-25% of glomerular capillary vessels; grade 2: Damage was observed in 26-50% of glomerular capillary vessels; grade 3: Damage was observed in 51-75% of glomerular capillary vessels; grade 4: Damage was observed in 76% and more of glomerular capillary vessels.

To evaluate the morbidity of interstitial fibrosis, the fibrotic area percentage of 10 regions per specimen was calculated on an image analyzer.

<Results>

(Evaluation Item 1: Blood Pressure)

The results are shown in FIG. 1. Blood pressure was expressed by the mean blood pressure as calculated from systolic and diastolic pressures ((systolic pressure−diastolic pressure)/3+diastolic pressure)). Lisinopril as an antihypertensive drug (ACE inhibitor) showed a certain level of blood pressure lowering action but compound A as a therapeutic drug for diabetes mellitus showed little blood pressure lowering action when dosed alone. On the other hand, a superior blood pressure lowering action was observed in the group dosed with the combination of compound A and lisinopril and this effect was quite marked as compared with the result in the group receiving independent dosing of lisinopril.

(Evaluation Item 2: Kidney Damage Score)

Glomerular Injury Score

Figure 2:
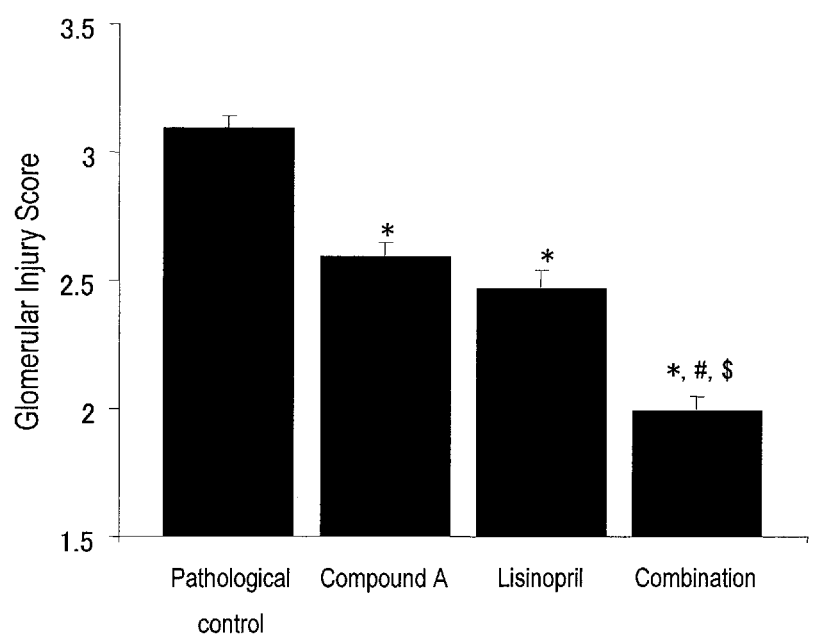
FIG. 2 compares how glomerular injury scores could be reduced by administering Compound A or lisinopril alone, or administering Compound A and lisinopril in combination.

The results are shown in FIG. 2. The animal model used in this experiment was in an advanced stage of kidney tissue injury resulting from a long-continued diabetic condition. In this animal model with kidney damage, compound A proved effective in improving scores of glomerular damage and so did lisinopril. The group dosed with the combination of compound A and lisinopril was even more marked in an improvement of scores of glomerular damage than the groups dosed with compound A and lisinopril administered independently.

Renocortical Fibrosis Score

Figure 3:
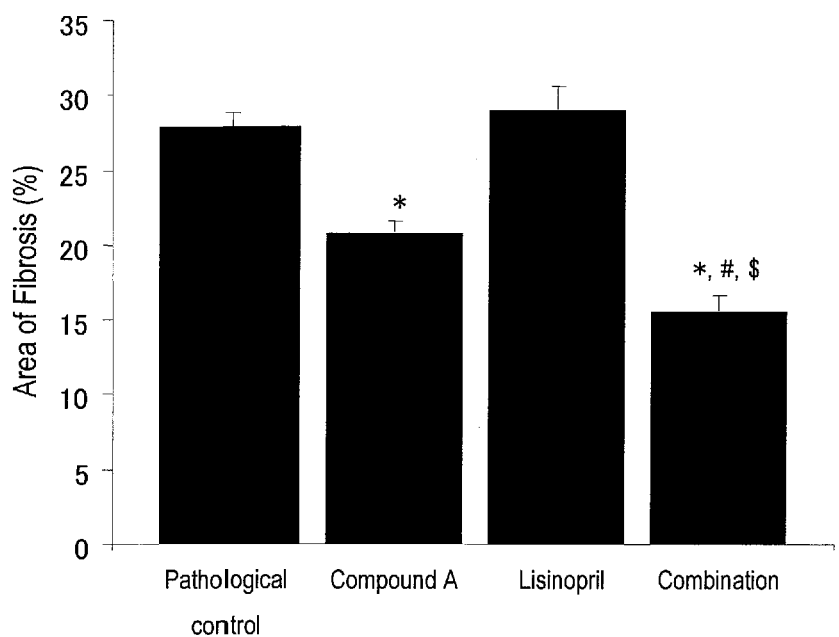
FIG. 3 compares how renal cortex fibrosis scores could be reduced by administering Compound A or lisinopril alone, or administering Compound A and lisinopril in combination.

The results are shown in FIG. 3. Compound A proved effective in ameliorating kidney tissue damage as evaluated by the area of kidney interstitial fibrosis. On the other hand, no improvement in the area of interstitial fibrosis was observed in the group receiving independent dosing of lisinopril. Nevertheless, the group dosed with the combination of compound A and lisinopril was even more marked in an improvement of scores of renocortical fibrosis than the groups dosed with compound A and lisinopril administered independently.

Drugs used to suppress the lowering of renal function should preferably have the ability to suppress the progress of glomerular damage and renocortical fibrosis as well. The simultaneous dosing of compound A and lisinopril could exhibit this preferred effect.

The above test results would be explained by the inhibition of SGLT2-mediated sugar uptake, which eventually affected the regulation of the activity of the renin-angiotensin-aldosterone system. Hence, similar results would be obtained even if other ACE inhibitors or angiotensin II receptor blockers are used. This can be verified by conducting the following test using an angiotensin II receptor blocker such as valsartan. In the test described below, it is expected that a superior blood pressure lowering action will be exhibited in a group dosed with the combination of compound A and valsartan and that the effect will be more marked than in a group receiving independent dosing of valsartan.

<Test 2: Diabetic Animal Model>

<Test Item>

The effect of compound A combined with angiotensin II receptor blocker in rats as a diabetic model.

<Test Method>

Goto-Kakizaki (GK) rats as model animals spontaneously manifesting non-obese diabetes mellitus (Japan SLC, Inc.) were fed a high-glucose diet containing compound A. During the feeding of compound A in a mixed diet, a vehicle or an angiotensin II receptor blocker was orally administered in a single dose and the effects of the two drugs, administered either independently or in combination, on blood pressure were studied by the crossover method. The systolic blood pressure was measured by the tail cuff method using a non-heated, noninvasive hemodynamometer immediately before the oral administration of the angiotensin II receptor blocker and 1, 2, 4, and 6 hours after such administration.

<Results>

Figure 4:
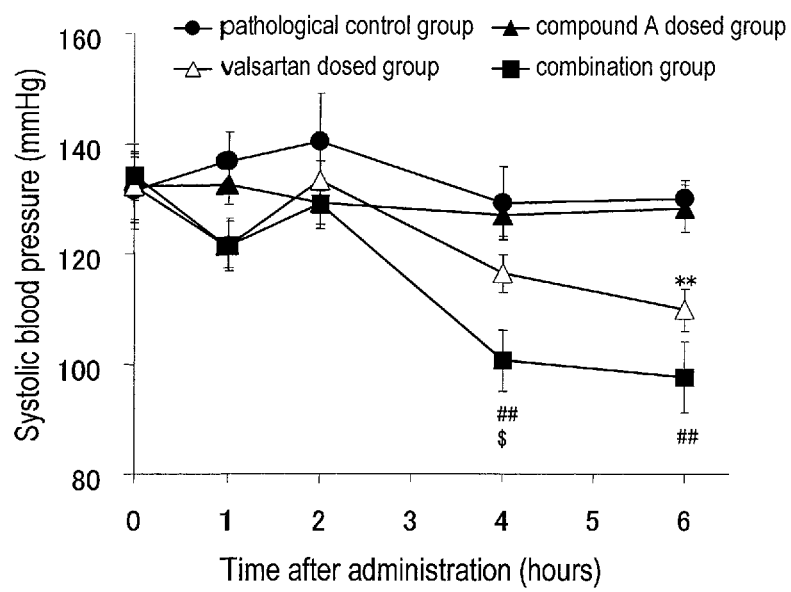
FIG. 4 compares how hypertension could be alleviated by administering Compound A or valsartan alone, or administering Compound A and valsartan in combination.

The results are shown in FIG. 4. Valsartan, an antihypertensive drug (angiotensin II receptor blocker), exhibited a certain level of action for lowering the systolic blood pressure but Compound A, a drug for treating diabetes mellitus, displayed little blood lowering action when administered alone. In contrast, the group administered with the combination of Compound A and valsartan showed a superior blood lowering action, which was a marked effect in comparison with the group administered with valsartan alone.

INDUSTRIAL APPLICABILITY

The present invention provides medicaments useful in the treatment of diseases involving at least hypertension or diabetes mellitus as a risk factor of cardiovascular events, or methods of treating the diseases. Since the present invention exhibits a superior hypotensive action that cannot be attained by any single antihypertensive drugs, the conventional problems associated with the use of two or more antihypertensive drugs in order to lower the blood pressure to the desired level can be solved. In addition, the present invention shows a marked therapeutic efficacy in diabetes mellitus, a disease associated with diabetes mellitus, or complications of diabetes mellitus, in particular, diabetic nephropathy. As a further advantage, the present invention is also useful for the treatment of diseases involving lowered renal function.

The invention claimed is:

1. A method for treating a disease involving at least hypertension or diabetes mellitus as a risk factor of cardiovascular events, which comprises administering (i) an SGLT2 inhibitor which is (1S)-1,5-anhydro-1-[3-(4-ethoxybenzyl)-6-methoxy-4-methylphenyl]-1-thio-D-glucitol, a pharmaceutically acceptable salt thereof, a hydrate of the compound or salt, and (ii) an antihypertensive compound selected from the group consisting of lisinopril and valsartan, or a pharmaceutically acceptable salt thereof, or a hydrate of the compound or salt, either simultaneously or separately, to a patient in need thereof.

2. The method according to claim 1, wherein the disease is hypertension.

3. The method according to claim 1, wherein the disease is diabetes mellitus, a disease associated with diabetes mellitus, or a complication of diabetes mellitus.

4. The method according to claim 1, wherein the disease involves manifestations of both diabetes mellitus and hypertension.

5. The method according to claim 1, wherein the disease is diabetic nephropathy.

6. The method according to claim 1, wherein the disease further involves an observable lowered renal function.

7. A method for enhancing the hypotensive action of an antihypertensive compound selected from the group consisting of lisinopril and valsartan, or a pharmaceutically acceptable salt thereof, or a hydrate of the compound or salt, which comprises administering an SGLT 2 inhibitor which is (1S)-1,5-anhydro-1-[3-(4-ethoxybenzyl)-6-methoxy-4-methylphenyl]-1-thio-D-glucitol, a pharmaceutically acceptable salt thereof, or a hydrate of the compound or salt, in combination with the antihypertensive compound.

8. A method for enhancing the effect of an SGLT 2 inhibitor which is (1S)-1,5-anhydro-1-[3-(4-ethoxybenzyl)-6-methoxy-4-methylphenyl]-1-thio-D-glucitol, a pharmaceutically acceptable salt thereof, or a hydrate of the compound or salt in treating diabetes mellitus, a disease associated with diabetes mellitus, or a complication of diabetes mellitus which comprises administering the SGLT 2 inhibitor in combination with an antihypertensive compound selected from the group consisting of lisinopril and valsartan, or a pharmaceutically acceptable salt thereof, or a hydrate of the compound or salt.

9. A method for enhancing the effect of an SGLT 2 inhibitor which is (1S)-1,5-anhydro-1-[3-(4-ethoxybenzyl)-6-methoxy-4-methylphenyl]-1-thio-D-glucitol, a pharmaceutically acceptable salt thereof, or a hydrate of the compound or salt in treating diabetic nephropathy which comprises administering the SGLT 2 inhibitor in combination with an antihypertensive compound selected from the group consisting of lisinopril and valsartan, or a pharmaceutically acceptable salt thereof, or a hydrate of the compound or salt.

* * * * *